US00PP24145P2

(12) United States Plant Patent
Shishido

(10) Patent No.: US PP24,145 P2
(45) Date of Patent: Jan. 7, 2014

(54) ***DIANTHUS* PLANT NAMED 'SHISHIKA-01'**

(50) Latin Name: *Dianthus speciosus*
Varietal Denomination: Shishika-01

(75) Inventor: Kazuyuki Shishido, Yokoshibahikari-machi (JP)

(73) Assignee: Amerinova Properties LLC, Bonsall, CA (US)

( * ) Notice: Subject to any disclaimer, the term of this patent is extended or adjusted under 35 U.S.C. 154(b) by 98 days.

(21) Appl. No.: 13/385,287

(22) Filed: Feb. 10, 2012

(51) Int. Cl.
*A01H 5/00* (2006.01)

(52) U.S. Cl.
USPC ..... Plt./282; Plt./272

(58) Field of Classification Search
USPC ..... Plt./282, 272
See application file for complete search history.

*Primary Examiner* — Susan McCormick Ewoldt
(74) *Attorney, Agent, or Firm* — C. A. Whealy

(57) ABSTRACT

A new and distinct cultivar of *Dianthus* plant named 'Shishika-01', characterized by its upright and mounding plant habit; moderately vigorous growth habit; short internodes and freely branching habit; red purple-colored flowers with white-colored centers that are positioned above the foliar plane; and good garden performance.

1 Drawing Sheet

Botanical designation: *Dianthus speciosus*.
Cultivar denomination: 'SHISHIKA-01'.

BACKGROUND OF THE INVENTION

The present invention relates to a new and distinct cultivar of *Dianthus* plant, botanically known as *Dianthus speciosus*, grown as a garden plant and hereinafter referred to by the name 'Shishika-01'.

The new *Dianthus* plant is a product of a planned breeding program conducted by the Inventor in Chiba, Japan. The objective of the breeding program was to develop new freely-branching and freely-branching *Dianthus* plants with attractive flower coloration.

The new *Dianthus* plant is a naturally-occurring whole plant mutation of *Dianthus speciosus* 'Kahori', not patented. The new *Dianthus* plant was discovered and selected by the Inventor as a single flowering plant from within a population of plants of 'Kahori' in a controlled greenhouse environment in Chiba, Japan in November, 2006.

Asexual reproduction of the new *Dianthus* plant by terminal cuttings propagated in a controlled environment in Chiba, Japan since December, 2006 has shown that the unique features of this new *Dianthus* plant are stable and reproduced true to type in successive generations of asexual reproduction.

SUMMARY OF THE INVENTION

Plants of the new *Dianthus* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Shishika-01'. These characteristics in combination distinguish 'Shishika-01' as a new and distinct *Dianthus* plant:

1. Upright and mounding plant habit.
2. Moderately vigorous growth habit.
3. Short internodes and freely branching habit.

4. Red purple-colored flowers with white-colored centers that are positioned above the foliar plane.
5. Good garden performance.

Plants of the new *Dianthus* differ from plants of the mutation parent, 'Kahori', primarily in plant habit as plants of the new *Dianthus* are more vigorous than and not as compact as plants of 'Kahori'. In addition, plants of the new *Dianthus* and 'Kahori' differ slightly in flower color.

Plants of the new *Dianthus* can be compared to plants of the *Dianthus speciosus* 'Shishi-01', disclosed in U.S. Plant patent application Ser. No. 12/069,042, now abandoned. In side-by-side comparisons conducted in Chiba, Japan, plants of the new *Dianthus* differed from plants of 'Shishi-01' in the following characteristics:

1. Plants of the new *Dianthus* were larger than and not as compact as plants of 'Shishi-01'.
2. Plants of the new *Dianthus* were more vigorous than plants of 'Shishi-01'.
3. Plants of the new *Dianthus* were more freely branching than plants of 'Shishi-01'.
4. Plants of the new *Dianthus* and 'Shishi-01' differed in flower color.

BRIEF DESCRIPTION OF THE PHOTOGRAPHS

The accompanying photographs illustrate the overall appearance of the new *Dianthus* plant showing the colors as true as it is reasonably possible to obtain in colored reproductions of this type. Colors in the photographs may differ slightly from the color values cited in the detailed botanical description which accurately describe the colors of the new *Dianthus* plant.

The photograph at the bottom of the sheet comprises a side perspective view of typical flowering plants of 'Shishika-01' grown in a container.

The photograph at the top of the sheet is a close-up view of a typical flowering plant of 'Shishika-01'.

DETAILED BOTANICAL DESCRIPTION

The aforementioned photographs and following observations and measurements describe plants grown during the summer in 16.5-cm containers in a polyethylene-covered greenhouse in Bonsall, Calif. under environmental conditions and cultural practices which approximate those generally used in commercial *Dianthus* production. During the production of the plants, day temperatures ranged from 29° C. to 37° C., night temperatures ranged from 18° C. to 21° C. and light levels averaged 5,000 foot-candles. Plants were pinched one time and were two months old when the photographs and the detailed description were taken. In the following description, color references are made to The Royal Horticultural Society Colour Chart, 2007 Edition, except where general terms of ordinary dictionary significance are used.

Botanical classification: *Dianthus speciosus* 'Shishika-01'.

Parentage: Naturally-occurring whole plant mutation of *Dianthus speciosus* 'Kahori', not patented.

Propagation:

*Type.*—Terminal cuttings.

*Time to initiate roots, summer.*—About two to three weeks at 22° C. to 27° C.

*Time to initiate roots, winter.*—About three to four weeks at 18° C. to 23° C.

*Time to produce a rooted young plant, summer.*—About four weeks at 22° C. to 27° C.

*Time to produce a rooted young plant, winter.*—About six weeks at 18° C. to 23° C.

*Root description.*—Medium thickness, fibrous; white in color.

*Rooting habit.*—Moderate branching; medium density.

Plant description:

*Plant and growth habit.*—Upright and mounding plant habit; freely clumping; vigorous growth habit.

*Plant height* (*soil level to top of flowers*).—About 13.5 cm.

*Plant height* (*soil level to top of foliar plane*).—About 9 cm.

*Plant diameter* (*spread*).—About 18 cm.

*Lateral branch description.*—Branching habit: Freely-branching growth habit with about 48 lateral branches developing per plant; pinching enhances lateral branch development; dense and bushy growth habit. Length: About 7.5 cm. Diameter: About 1.5 mm. Internode length: About 9 mm. Texture: Smooth, glabrous. Color: Close to 145A; with development, color becoming closer to 199A.

*Foliage description.*—Arrangement: Opposite, simple. Length: About 4.2 cm. Width: About 3 mm. Shape: Lanceolate. Apex: Acute. Base: Attenuate. Margin: Entire. Texture, upper and lower surfaces: Smooth, glabrous. Venation pattern: Parallel. Color: Developing leaves, upper surface: Close to 137B. Developing leaves, lower surface: Close to 137C. Fully expanded leaves, upper surface: Close to N137C; venation, close to N137C. Fully expanded leaves, lower surface: Close to 137A; venation, 137C. Petioles: Length: About 3 mm. Diameter: About 2 mm. Texture, upper and lower surfaces: Smooth, glabrous. Color, upper and lower surfaces: Close to 145B.

Flower description:

*Flower type and flowering habit.*—Single rotate terminal and axillary flowers; freely flowering with typically two flowers developing per lateral shoot; flowers positioned above the foliar plane; flowers face upright.

*Fragrance.*—Faintly fragrant; clove-like.

*Natural flowering season.*—Flowering is continuous during the spring in Southern California; plants begin flowering about six to eight weeks after planting.

*Flower longevity.*—Flowers last about four to five days on the plant; flowers persistent.

*Flower diameter.*—About 3 cm.

*Flower depth.*—About 2.7 cm.

*Flower buds.*—Length: About 2.3 cm. Diameter: About 5 mm. Shape: Oblong. Color: Close to 75B to 75C.

*Petals.*—Quantity and arrangement: About five arranged in a single whorl. Length: About 3 cm. Width: About 1.5 cm. Shape: Roughly obdeltoid. Apex: Rounded; praemorse. Base: Attenuate. Margin: Entire. Texture, upper and lower surfaces: Smooth, glabrous; velvety. Color: When opening, upper surface: Close to 71C. When opening, lower surface: Close to 75A. Fully opened, upper surface: Close to 71B; towards the base, close to 157C to 157D. Fully opened, lower surface: Close to 73A.

*Sepals.*—Quantity and arrangement: Five fused arranged in a single whorl. Length: About 1.5 mm. Width: About 2 mm. Shape: Lanceolate. Apex: Acuminate. Margin: Entire. Texture, upper and lower surfaces: Smooth, glabrous. Color, upper surface: Close to 147C. Color, lower surface: Close to 146A.

*Peduncles.*—Length: About 3.5 cm. Diameter: About 1 mm. Strength: Strong. Texture: Smooth, glabrous. Color: Close to 137A.

*Reproductive organs.*—Stamens: Quantity: About ten per flower. Filament length: About 1.1 cm. Filament color: Close to NN155D. Anther length: About 2 mm. Anther shape: Oblong. Anther color: Close to 156A. Pollen amount: Scarce. Pollen color: Close to 156C. Pistils: Quantity: One per flower. Pistil length: About 1.5 cm. Stigma shape: Bi-parted. Stigma color: Close to 85C. Style length: About 6 mm. Style color: Close to 85D. Ovary color: Close to 145C.

*Seeds and fruits.*—Seed and fruit development have not been observed on plants of the new *Dianthus*.

Disease & pest resistance: Plants of the new *Dianthus* have not been observed to be resistant to pathogens and pests common to *Dianthus* plants.

Garden performance: Plants of the new *Dianthus* have been observed to have good garden performance and to tolerate wind, rain and temperatures ranging from about 1° C. to 35° C.

It is claimed:

1. A new and distinct *Dianthus* plant named 'Shishika-01' as illustrated and described.

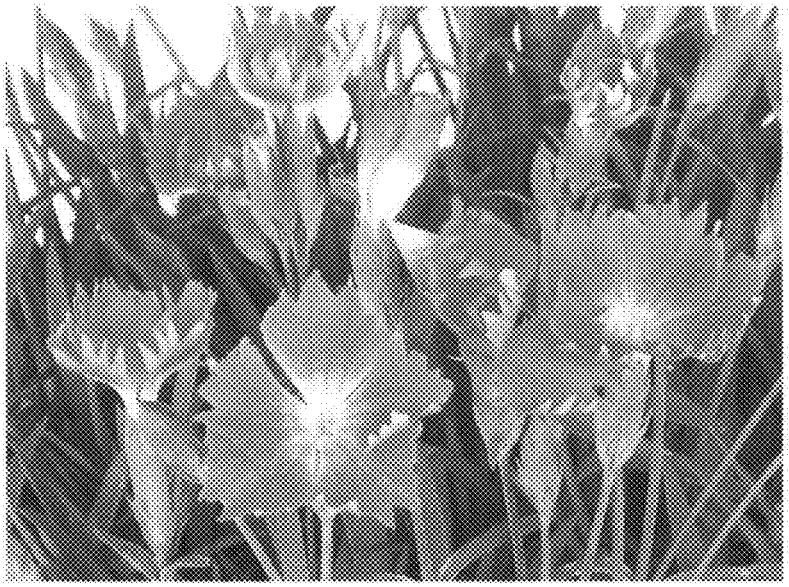
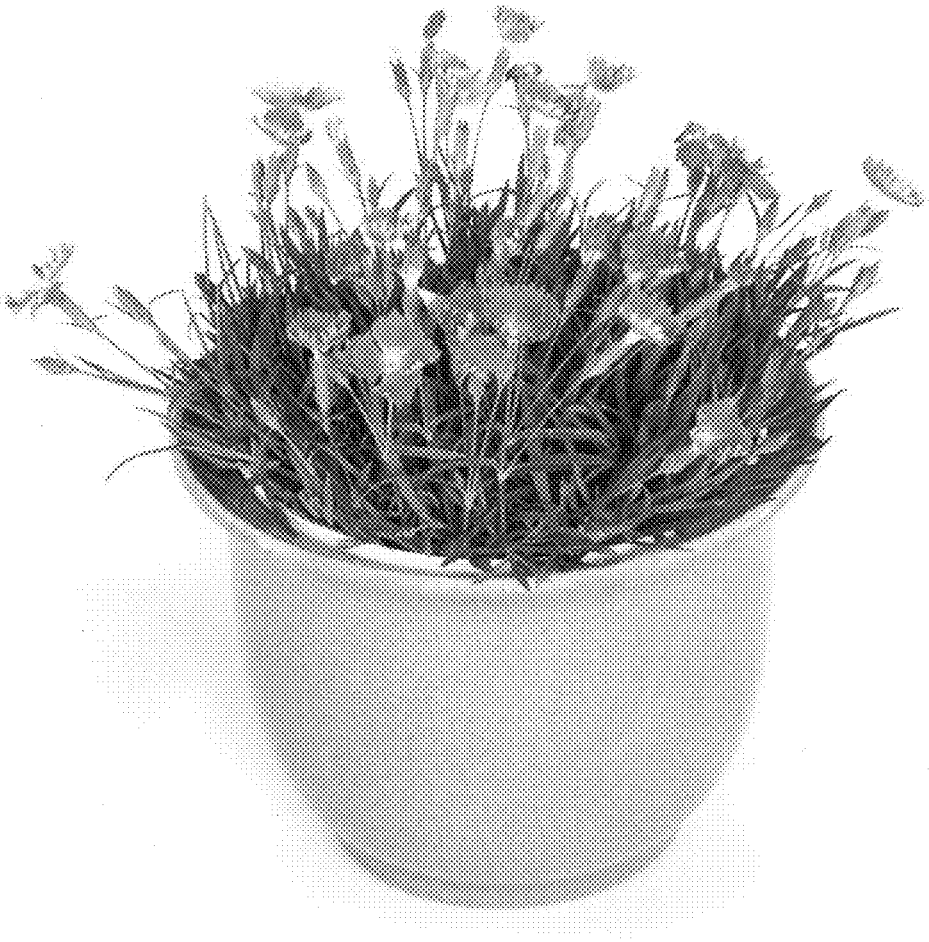

* * * * *